United States Patent
Ichioka et al.

(10) Patent No.: US 7,985,182 B2
(45) Date of Patent: Jul. 26, 2011

(54) ULTRASONIC DIAGNOSTIC APPARATUS AND ULTRASONIC IMAGE ACQUIRING METHOD

(75) Inventors: Kenichi Ichioka, Nasushiobara (JP); Muneki Kataguchi, Nasushiobara (JP); Fumiyasu Sakaguchi, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 602 days.

(21) Appl. No.: 11/335,668

(22) Filed: Jan. 20, 2006

(65) Prior Publication Data

US 2006/0184031 A1 Aug. 17, 2006

(30) Foreign Application Priority Data

Jan. 26, 2005 (JP) ................................. 2005-018172
Dec. 20, 2005 (JP) ................................. 2005-366203

(51) Int. Cl.
*A61B 8/00* (2006.01)

(52) U.S. Cl. ........................ 600/444; 600/445; 600/447

(58) Field of Classification Search .................. 600/437, 600/443–447

See application file for complete search history.

(56) References Cited

U.S. PATENT DOCUMENTS

| | | | |
|---|---|---|---|
| 4,399,822 A * | 8/1983 | Theumer | 600/445 |
| 5,456,256 A * | 10/1995 | Schneider et al. | 600/445 |
| 5,497,776 A | 3/1996 | Yamazaki et al. | |
| 5,540,229 A | 7/1996 | Collet-Billon et al. | |
| 5,605,155 A * | 2/1997 | Chalana et al. | 600/443 |
| 6,544,178 B1 | 4/2003 | Grenon et al. | |
| 6,638,220 B2 * | 10/2003 | Satoh | 600/437 |
| 6,656,120 B2 | 12/2003 | Lee et al. | |
| 2002/0133075 A1 | 9/2002 | Abdelhak | |
| 2003/0060700 A1 | 3/2003 | Solf et al. | |
| 2004/0024302 A1 * | 2/2004 | Chalana et al. | 600/407 |

(Continued)

FOREIGN PATENT DOCUMENTS

JP 7-222742 8/1995

(Continued)

OTHER PUBLICATIONS

Japanese Office Action issued Feb. 22, 2011, in Patent Application No. 2005-366203.

*Primary Examiner* — Long V Le
*Assistant Examiner* — Angela M Hoffa
(74) *Attorney, Agent, or Firm* — Oblon, Spivak, McClelland, Maier & Neustadt, L.L.P.

(57) ABSTRACT

A measurement data processing device measures a size of a diagnostic region from a tomographic image as two-dimensional information. An ROI width determining device determines a size of a region of interest based on the size (lateral width and longitudinal width) of the diagnostic region. An oscillation angle determining device determines a range of an angle for oscillating ultrasonic transducers based on the size. An oscillation rate determining device determines a rate for oscillating the ultrasonic transducers based on information indicating the oscillation angle and image quality. In order to acquire a three-dimensional image of the diagnostic region, the probe oscillation control device controls the oscillation of the ultrasonic transducers based on the information. A three-dimensional image processing device extracts a three-dimensional image of in the determined region of interest from the acquired three-dimensional image. A display device displays the extracted three-dimensional image. Then, the three-dimensional image based on the shape of the diagnostic region is acquired.

20 Claims, 10 Drawing Sheets

U.S. PATENT DOCUMENTS

| | | |
|---|---|---|
| 2004/0106869 A1 | 6/2004 | Tepper |
| 2005/0054921 A1* | 3/2005 | Katsman et al. .............. 600/437 |

FOREIGN PATENT DOCUMENTS

| | | |
|---|---|---|
| JP | 11-113901 | 4/1999 |
| JP | 2000-197631 | 7/2000 |
| JP | 2002-153473 | 5/2002 |
| JP | 2003-275204 | 9/2003 |
| JP | 2004-275223 | 10/2004 |
| JP | 2004-313652 | 11/2004 |
| JP | 2004-344517 | 12/2004 |
| JP | 2006-231035 | 9/2006 |
| WO | WO 2004/112577 A3 | 12/2004 |

* cited by examiner

TWO-DIMENSIONALLY
ARRANGED TRANSDUCERS

OSCILLATION DIRECTION

OSCILLATION DIRECTION

OSCILLATION DIRECTION

FIG. 8

|  |  | RANGE OF OSCILLATION ANGLE | | | | | |
| --- | --- | --- | --- | --- | --- | --- | --- |
|  |  | 20° | 25° | 30° | 35° | 40° | 45° |
| IMAGE QUALITY | HIGH QUALITY | 40 | 50 | 60 | 70 | 80 | 90 |
| | INTERMEDIATE QUALITY | 60 | 70 | 80 | 90 | 100 | 110 |
| | LOW QUALITY | 80 | 90 | 100 | 110 | 120 | 130 |

ULTRASONIC DIAGNOSTIC APPARATUS AND ULTRASONIC IMAGE ACQUIRING METHOD

BACKGROUND OF THE INVENTION

1. Field of the Invention

The present invention relates to an ultrasonic diagnostic apparatus capable of acquiring a three-dimensional image, and more particularly to an ultrasonic diagnostic apparatus for extracting a three-dimensional image of a region of interest.

2. Description of the Related Art

An image diagnostic apparatus such as an X-ray diagnostic apparatus, an X-ray CT apparatus, an MRI apparatus, or an ultrasonic diagnostic apparatus is used as an apparatus for taking an image of an internal portion of an object to be examined. Of the image diagnostic apparatuses described above, the ultrasonic diagnostic apparatus has a small size and is noninvasive. In addition, there is no X-ray exposure to the object to be examined. Therefore, the ultrasonic diagnostic apparatus is used for, for example, the diagnosis of the development of an unborn baby.

As shown in a perspective view of FIG. 1A, an ultrasonic probe provided to the ultrasonic diagnostic apparatus includes ultrasonic transducers 21 which are one-dimensionally arranged in a scanning direction (X-direction). Ultrasonic transmission and reception is performed within an X-Z plane by electronic delay control to acquire a tomographic image (two-dimensional image) of the object to be examined. Here, the ultrasonic probe including the one-dimensionally arranged ultrasonic transducers is referred to as a "one-dimensional ultrasonic probe" for the sake of convenience.

In recent years, an ultrasonic diagnostic apparatus capable of performing not only the taking of a two-dimensional tomographic image but also the taking and displaying of a three-dimensional image has been put to practical use and is using in the clinical field. In the ultrasonic diagnostic apparatus, the one-dimensional ultrasonic probe including an oscillation mechanism is mechanically moved to acquire a plurality of tomographic images along a direction (oscillation direction) orthogonal to the scanning direction. A three-dimensional image is generated based on the acquired tomographic images. For example, in the ultrasonic diagnostic apparatus, the one-dimensionally arranged ultrasonic transducers 21 are mechanically oscillated in the direction (Y-direction) orthogonal to the scanning direction (X-direction) to acquire a plurality of tomographic images along the oscillation direction (Y-direction). A three-dimensional image is generated based on the acquired tomographic images. Hereinafter, a plane along the direction in which the ultrasonic transducers 21 are arranged is referred to as a "scanning plane". The scanning plane is a plane parallel to the scanning direction (X-direction).

As shown in FIG. 1B, development is being made on an ultrasonic probe in which ultrasonic transducers are two-dimensionally arranged to scan a three-dimensional image taking region with an ultrasonic wave, thereby obtaining a three-dimensional image. Here, the ultrasonic probe in which the ultrasonic transducers are two-dimensionally arranged is referred to as a "two-dimensional ultrasonic probe" for the sake of convenience.

In the ultrasonic diagnostic apparatus, ultrasonic transmission and reception is performed on a diagnostic region by using the ultrasonic probe capable of acquiring the three-dimensional image as described above to acquire a three-dimensional image of the diagnostic region. For example, when a three-dimensional image of a head of an unborn baby is to be acquired, a region of interest (ROI) which includes the head of the unborn baby is set in order to display an image of the entire head of the unborn baby. The three-dimensional image in the set region of interest (ROI) is displayed on the ultrasonic diagnostic apparatus.

Up to now, the region of interest (ROI) is set by an operator. For example, before the three-dimensional image is acquired by the ultrasonic diagnostic apparatus, the operator has determined setting conditions (parameters) such as an angle range for oscillating the ultrasonic transducers, an oscillation rate, and a size of the region of interest (ROI), and inputted the setting conditions (parameters) to the ultrasonic diagnostic apparatus. The ultrasonic diagnostic apparatus has extracted image data included in the region of interest (ROI) based on the inputted setting conditions (for example, JP 2003-275204 A).

However, because the operator has determined the setting conditions (parameters) as to the region of interest (ROI), there have been the following problems. When the angle for oscillating the ultrasonic transducers is insufficient in some setting contents, an image of an entire desirable diagnostic region could not be acquired. When the oscillation rate is too high, an image acquired has become rougher, so that a preferable image has not been obtained. When a width of the region of interest (ROI) is too large, unnecessary data has been acquired to leave an unnecessary image of a region located before the desirable diagnostic region, with the result that the image of the entire diagnostic region has not displayed. For example, when a three-dimensional image of an unborn baby is to be acquired, the three-dimensional image of the entire face of the unborn baby could not be obtained, or an unnecessary image of a region located before the face of the unborn baby is left, so that the image of the entire face has not been displayed.

As described above, it is difficult for even a skilled operator to extract the three-dimensional image of the region of interest (ROI) by the ultrasonic diagnostic apparatus and display the extracted three-dimensional image thereon. When the image of the entire desirable diagnostic region cannot be preferably displayed, until it is preferably displayed, it is necessary to input the setting conditions including the oscillation angle range to the ultrasonic diagnostic apparatus many times by the operator to set the region of interest (ROI), thereby performing the image taking many times. Therefore, there has been a problem in that a time required for examination performed by the ultrasonic diagnostic apparatus becomes longer.

SUMMARY OF THE INVENTION

An object of the present invention is to provide an ultrasonic diagnostic apparatus capable of automatically determining setting conditions of a region of interest (ROI) for extracting a three-dimensional image based on information as to an object to be examined to omit an input operation of the setting conditions which is performed by an operator, thereby reducing a frequency of resetting. Therefore, an object of the present invention is to provide an ultrasonic diagnostic apparatus capable of reducing an examination time to reduce burdens on a patient and the operator.

According to a first aspect of the present invention, there is provided an ultrasonic diagnostic apparatus, including: a condition determining device for determining a three-dimensional image taking region set with an ultrasonic wave in an object to be examined based on information of the object to be examined; and a scanning device for scanning the object to be examined with the ultrasonic wave in the determined three-dimensional image taking region to acquire a three-dimensional ultrasonic image.

According to the first aspect, the three-dimensional image taking region is determined based on the information of the object to be examined, so that it is possible to extract the three-dimensional ultrasonic image in a region suitable for the object to be examined. Therefore, an input operation of setting conditions which is performed by the operator can be omitted and the frequency of the resetting which is performed by the operator can be reduced. As a result, an examination time in the case where the ultrasonic diagnostic apparatus is used can be shortened to reduce burdens on a patient and the operator.

Further, according to a second aspect of the present invention, the scanning device includes a plurality of ultrasonic transducers arranged in a predetermined direction, and the three-dimensional ultrasonic image is acquired by scanning the object to be examined with the ultrasonic wave in the three-dimensional image taking region while the ultrasonic transducers are oscillated in a direction orthogonal to a scanning plane corresponding to the predetermined direction. The condition determining device determines a size of a region of interest on the scanning plane an angle range for oscillating the ultrasonic transducers based on the information of the object to be examined. The scanning device acquires the three-dimensional ultrasonic image by scanning the object to be examined while the ultrasonic transducers are oscillated based on the determination.

According to the second aspect, the size of the region of interest and the angle range for oscillating the ultrasonic transducers are determined based on the information of the object to be examined, so that it is possible to extract the three-dimensional ultrasonic image in a region suitable for the size of the object to be examined. Therefore, the input operation of setting conditions which is performed by the operator can be omitted and the frequency of the resetting which is performed by the operator can be reduced.

Further, according to a third aspect of the present invention, the object to be examined includes a mother and an unborn baby. The condition determining device determines the size of the region of interest on the scanning plane based on a two-dimensional ultrasonic image including the mother and the unborn baby, which is acquired in advance by scanning the mother. The condition determining device determines the size of the region of interest and the angle range for oscillating the ultrasonic wave based on, for example, unborn development information obtained from the two-dimensional ultrasonic image including the mother and the unborn baby, the shape of the head of the unborn baby, or the size of the head of the unborn baby.

According to the third aspect, the size of the region of interest and the angle range for oscillating the ultrasonic transducers are determined based on information obtained from the two-dimensional ultrasonic image including the mother and the unborn baby which is acquired in advance, so that it is possible to extract the three-dimensional ultrasonic image in a region suitable for the size of the unborn baby. Therefore, the input operation of setting conditions which is performed by the operator can be omitted and the frequency of the resetting which is performed by the operator can be reduced.

BRIEF DESCRIPTION OF THE DRAWINGS

In the accompanying drawings:

FIG. 8 is a table for obtaining a rate for oscillating the ultrasonic transducers;

DETAILED DESCRIPTION OF THE EMBODIMENTS

Hereinafter, an ultrasonic diagnostic apparatus and an ultrasonic image acquiring method according to an embodiment of the present invention will be described with reference to FIGS. 1A and 1B to 10.

(Structure)

The ultrasonic diagnostic apparatus according to the embodiment of the present invention and an ultrasonic probe used therein will be described with reference to FIGS. 1A and 1B to 3.

Figure 3:
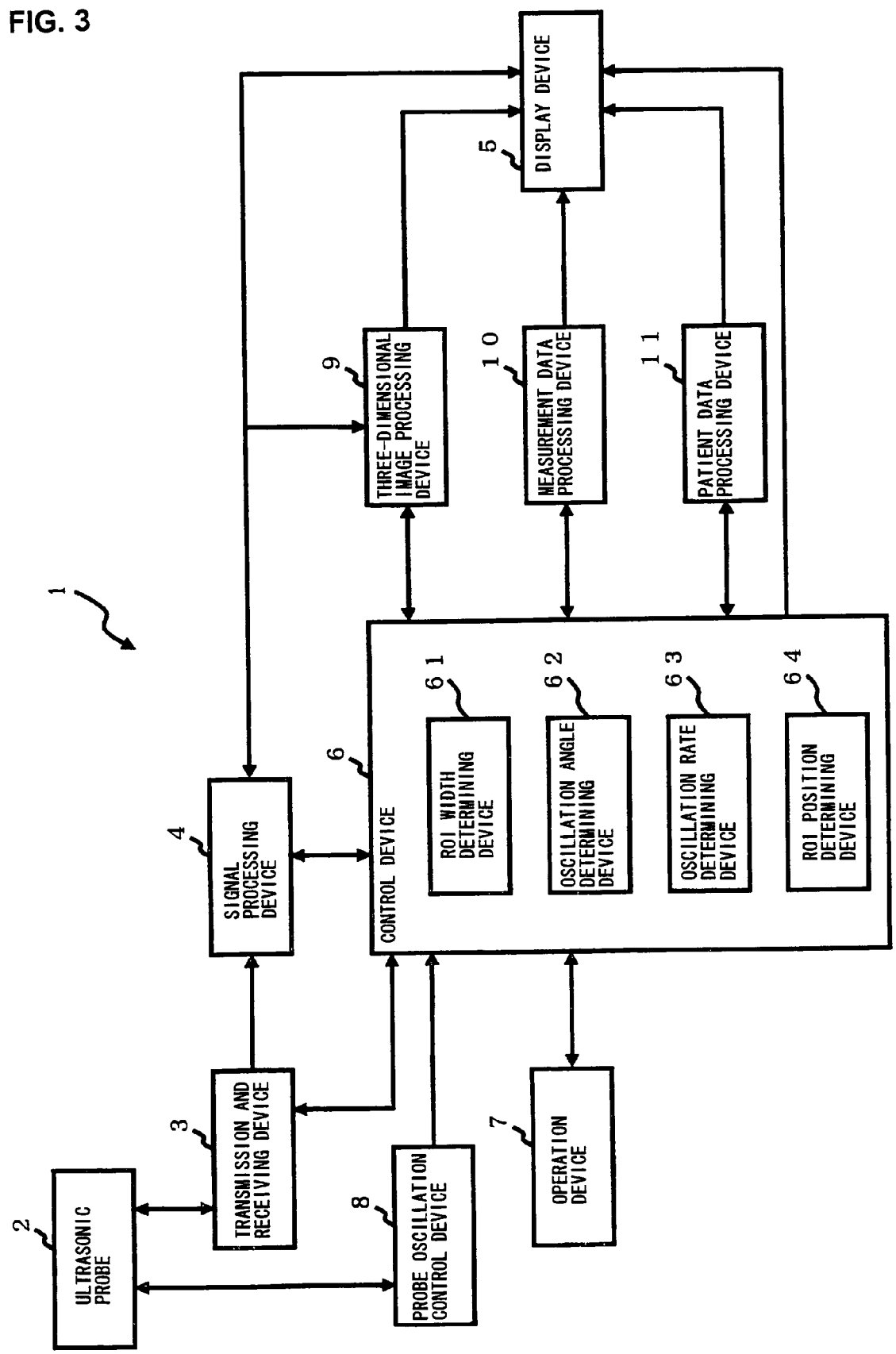
FIG. 3 is a block diagram showing a schematic structure of an ultrasonic diagnostic apparatus.
Figure 4:
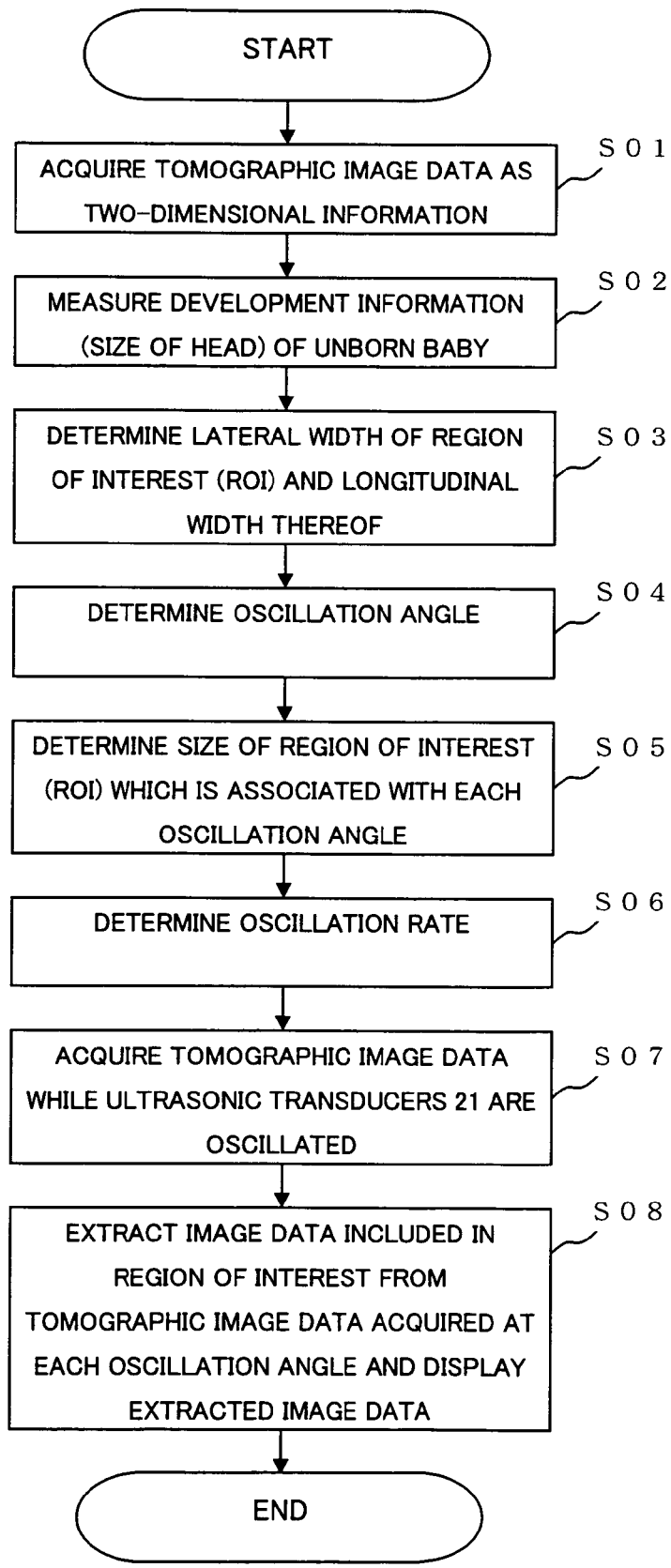
FIG. 4 is a flow chart for explaining a series of operations of the ultrasonic diagnostic apparatus.

As shown in FIG. 3, an ultrasonic diagnostic apparatus 1 according to this embodiment includes an ultrasonic probe 2, a transmission and receiving device 3, a signal processing device 4, a display device 5, a control device 6, an operation device 7, a probe oscillation control device 8, a three-dimensional image processing device 9, a measurement data processing device 10, and a patient data processing device 11.

Figure 1A:
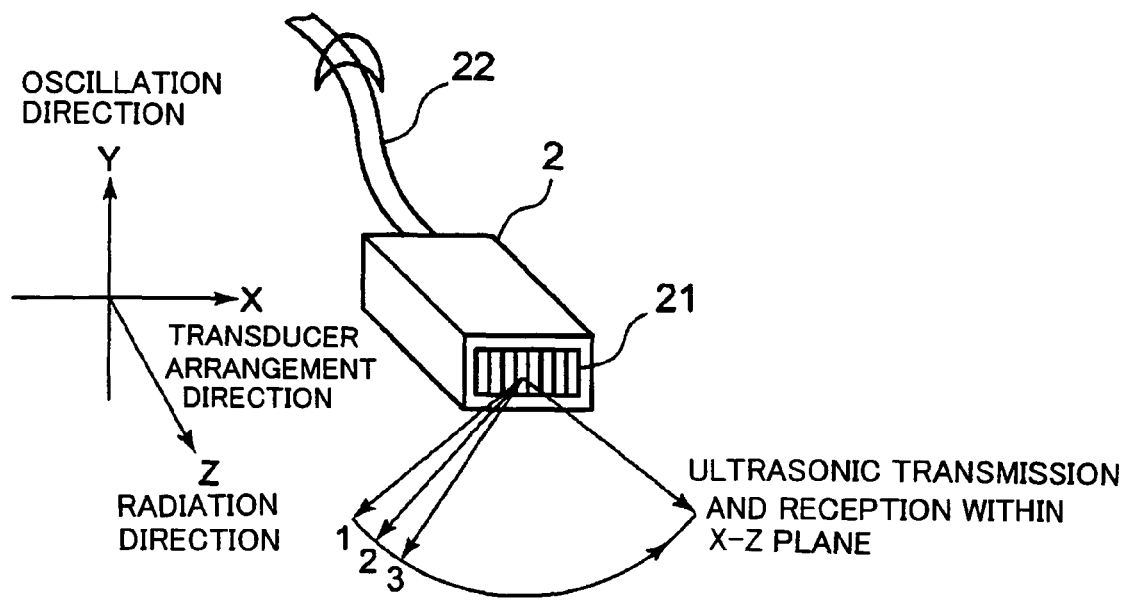
FIG. 1A is a perspective view showing a schematic structure of a conventional one-dimensional ultrasonic probe.
Figure 1B:
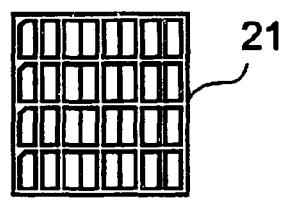
FIG. 1B is a plan view showing two-dimensionally arranged conventional ultrasonic transducers.
Figure 2A:
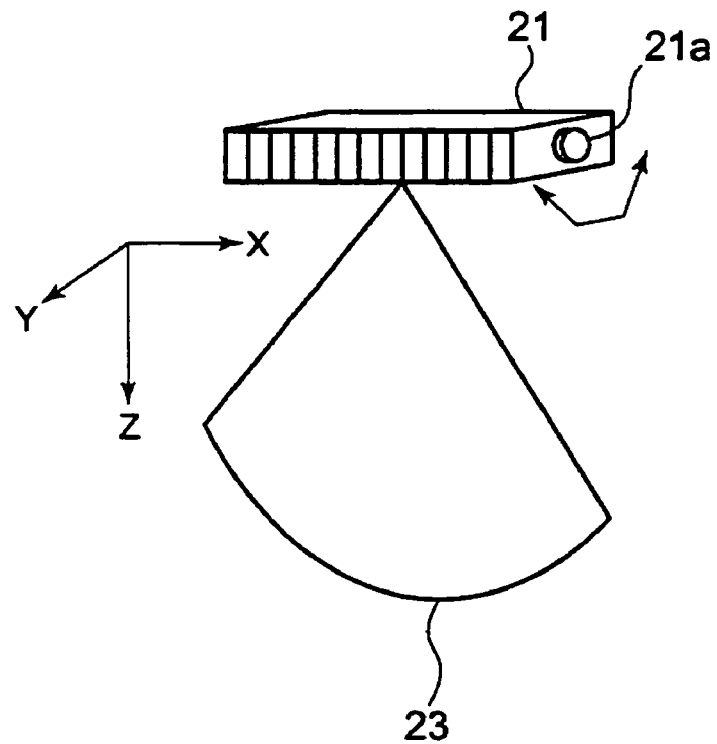
FIG. 2A is an explanatory view for an operation of the one-dimensional ultrasonic probe, which is a perspective view showing conventional ultrasonic transducers.
Figure 2B:
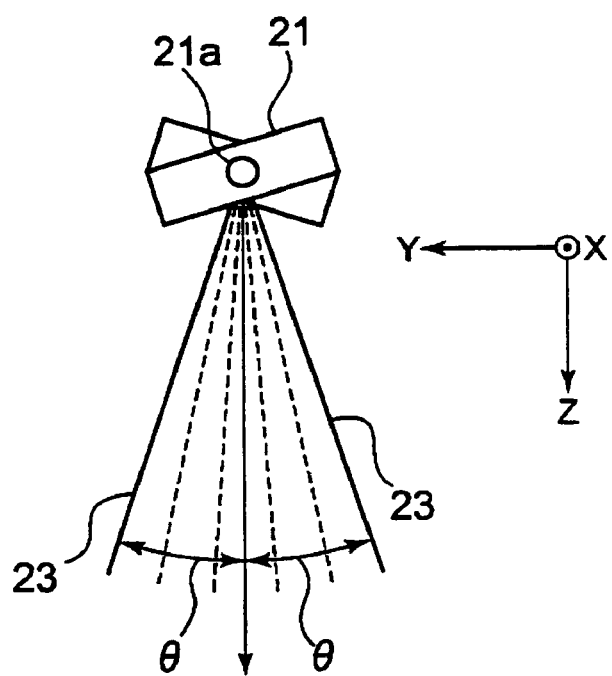
FIG. 2B is an explanatory view for the operation of the conventional one-dimensional ultrasonic probe, which is a side view showing the ultrasonic transducers.

The ultrasonic probe 2 to be used is the one-dimensional ultrasonic probe as shown in FIG. 1A or the two-dimensional ultrasonic probe as shown in FIG. 1B. The ultrasonic probe 2 is connected with a main body of the ultrasonic diagnostic apparatus 1 through a cable 22. In the one-dimensional ultrasonic probe as shown in FIG. 1A, ultrasonic transducers 21 are one-dimensionally arranged in a scanning direction (X-direction). A motor (not shown) is provided for the ultrasonic probe 2. In the ultrasonic diagnostic apparatus 1, the ultrasonic transducers 21 are oscillated in an oscillation direction (Y-direction) by the motor to acquire a plurality of tomographic images along the oscillation direction (Y-direction). The ultrasonic diagnostic apparatus 1 generates a three-dimensional image based on the acquired tomographic images. For example, as shown in FIGS. 2A and 2B, in the ultrasonic diagnostic apparatus 1, the ultrasonic transducers 21 which is one-dimensionally arranged are mechanically oscillated about an oscillation center point 21a in the direction (Y-direction) orthogonal to the scanning direction (X-direction). Therefore, while the ultrasonic transducers 21 are oscillated in a direction orthogonal to a scanning plane 23, the ultrasonic transmission and reception are performed. As shown in FIG. 2B, assume that an angle formed between the scanning plane 23 and the z-direction is expressed as an oscillation angle θ and a rate for oscillating the ultrasonic transducers 21 in the oscillation direction (Y-direction) is referred to as an oscillation rate.

When the ultrasonic probe 2 to be used is a two-dimensional ultrasonic probe in which ultrasonic transducers are arranged in a grid shape, the scanning plane 23 is electronically oscillated to acquire a three-dimensional image in the ultrasonic diagnostic apparatus 1.

The transmission and receiving device 3 includes a transmission unit and a receiving unit. The transmission and receiving device 3 supplies an electrical signal to the ultrasonic probe 2 to generate an ultrasound wave and receives an echo signal received by the ultrasonic probe 2.

The transmission unit of the transmission and receiving device 3 includes a clock generating circuit, a transmission delay circuit, and a pulser circuit. The clock generating circuit generates a clock signal for determining a transmission timing of an ultrasonic signal and a transmission frequency thereof. The transmission delay circuit performs transmission focusing with delay at the time of ultrasonic transmission. The pulser circuit has pulsers provided for separate paths (channels) corresponding to the number of the ultrasonic transducers. The pulser circuit generates drive pulses at delayed transmission timings and supplies the generated drive pulses to the respective ultrasonic transducers of the ultrasonic probe 2.

The receiving unit of the transmission and receiving device 3 includes a preamplifier, an A/D converter, and a reception delay and adding circuit. The preamplifier amplifies an echo signal outputted from each of the ultrasonic transducers of the ultrasonic probe 2 for each receiving channel. The A/D converter performs A/D conversion on the amplified echo signal. The reception delay and adding circuit delays the echo signals obtained after the A/D conversion with delay times necessary to determine receiving directivity and adds the delayed echo signals to one another. A reflection component from a direction corresponding to the receiving directivity is enhanced by the addition. A signal obtained by the addition in transmission and receiving device 3 is referred to as "RF data (raw data)".

The signal processing device 4 performs echo amplitude information visualization based on the RF data outputted from the transmission and receiving device 3 to generate B-mode ultrasonic raster data from the echo signals. More specifically, the signal processing device 4 performs band-pass filtering on the RF data. After that, the signal processing device 4 detects envelope curve data of an output signal obtained by the band-pass filtering and performs compression such as logarithmic conversion on the detected envelope curve data. Therefore, data whose signal strength is expressed by the intensity of brightness is generated. The signal processing device 4 further performs processing such as edge enhancement in some cases.

The signal processing device 4 converts the B-mode ultrasonic raster data which is expressed by a train of scanning line signals and obtained by the signal processing into coordinate system data based on spatial information (scanning conversion processing). In other words, in order to be able to display a train of signals which is obtained in synchronization with ultrasonic scanning on the display device 5 of a television scanning system, scanning system conversion is performed by reading the train of signals in synchronization with normal television scanning. Therefore, tomographic image data which is two-dimensional information, that is, so-called B-mode image data is generated. The tomographic image data is outputted to each of the display device 5 and the three-dimensional image processing device 9 and displayed as a two-dimensional tomographic image on a monitor screen of the display device 5.

The control device 6 is composed of a CPU and connected with each of the devices included in the ultrasonic diagnostic apparatus 1 to control the devices. The control device 6 includes a ROI width determining device 61, an oscillation angle determining device 62, an oscillation rate determining device 63, and a ROI position determining device 64. Note that the ROI width determining device 61, the oscillation angle determining device 62, the oscillation rate determining device 63, and the ROI position determining device 64 are corresponded to a condition determining device.

The ROI width determining device 61 determines a size of the region of interest (ROI) on the tomographic image (scanning plane 23) based on the tomographic image data (two-dimensional information) generated by the signal processing device 4 and one of unborn baby development information or unborn baby age information. For example, the ROI width determining device 61 determines a longitudinal width of the region of interest (ROI) and a lateral width thereof. The unborn baby development information corresponds to information indicating a size of the head of the unborn baby. The unborn baby age information corresponds to information indicating how the unborn baby is growing.

The oscillation angle determining device 62 determines a range of the oscillation angle θ for oscillating the ultrasonic transducers 21 based on the tomographic image data (two-dimensional information) generated by the signal processing device 4, one of the unborn baby development information or the unborn baby age information, and the size of the region of interest (ROI).

The oscillation rate determining device 63 determines the oscillation rate for oscillating the ultrasonic transducers 21 based on the range of the oscillation angle θ for oscillating the ultrasonic transducers 21 and information indicating image quality which is inputted from the operation device 7. The information indicating image quality corresponds to information which is determined by the operator and inputted from the operation device 7. A table in which the range of the oscillation angle, the information indicating image quality, and the oscillation rate are associated with one another is stored in advance in a memory device (not shown) provided in the ultrasonic diagnostic apparatus 1. The oscillation rate determining device 63 determines the oscillation rate with reference to the table.

The ROI position determining device 64 determines a position of the region of interest (ROI). The processing content of the ROI position determining device 64 will be described in detail later.

The operation device 7 is composed of a keyboard, a mouse, a trackball, or a touch command screen (TCS). The operation device 7 is connected with the control device 6. The setting conditions (setting parameters) of the region of interest (ROI) and commands for the ultrasonic diagnostic apparatus 1 are inputted from the operation device 7 to the control device 6 by the operator.

The probe oscillation control device 8 controls the oscillation angle of the ultrasonic probe 2 and the oscillation rate thereof based on the information of the oscillation angle θ and the information of the oscillation rate which are received from the control device 6. For example, when the ultrasonic probe 2 to be used is a one-dimensional ultrasonic probe, the probe oscillation control device 8 drives the motor (not shown) provided in the ultrasonic probe 2 to oscillate the ultrasonic transducers 21. At this time, the ultrasonic transducers 21 are oscillated by the probe oscillation control device 8 in the range of the oscillation angle outputted from the control device 6 at the oscillation rate outputted from the control device 6.

The three-dimensional image processing device 9 generates the three-dimensional image data included in the region of interest (ROI) based on the tomographic image data (two-dimensional information) generated by the signal processing device 4 and the information indicating the size of the region of interest (ROI) which is determined by the ROI width determining device 61. For example, when generating the three-dimensional image data using the one-dimensional ultrasonic probe, since a plurality of tomographic image data along the oscillation direction (Y-direction) are acquired due to the oscillation of the ultrasonic transducers 21 by the control of the probe oscillation control device 8. The plurality of tomographic image data is outputted from the signal processing device 4 to the three-dimensional image processing device 9. The three-dimensional image processing device 9 reconstructs three-dimensional image data from the plurality of tomographic image data. At the time of reconstruction, the three-dimensional image processing device 9 extracts the three-dimensional image data included in the region of interest (ROI) which is determined by the ROI width determining device 61. The three-dimensional image data extracted from the three-dimensional image processing device 9 is outputted to the display device 5 and displayed on the monitor screen of the display device 5.

The measurement data processing device 10 obtains the unborn baby development information from the tomographic image data (two-dimensional information) displayed on the monitor screen of the display device 5. When the tomographic image of the head of the unborn baby is being displayed on the monitor screen, the measurement data processing device 10 measures a size (including longitudinal width and lateral width) of the head of the unborn baby. For example, the measurement data processing device 10 measures a biparietal diameter and the like. The biparietal diameter is a diameter of a head portion having a longest lateral width when the head of the unborn baby is viewed from the above. Information indicating the size of the head of the unborn baby which is measured by the measurement data processing device 10 is outputted to each of the display device 5 and the control device 6. The outputted information is displayed on the monitor screen of the display device 5. The outputted information is used to determine, for example, the size of the region of interest (ROI) in the control device 6.

The patient data processing device 11 calculates an unborn baby age based on patient information of a mother which is inputted from the operation device 7 and outputs the calculated unborn baby age information to each of the display device 5 and the control device 6. The patient information of the mother corresponds to, for example, the last menstrual date of the mother. Therefore, the patient data processing device 11 calculates the unborn baby age from the last menstrual date. An unborn baby development state is apparent from the unborn baby age, so the patient data processing device 11 determines the size of the head of the unborn baby from the unborn baby age information.

The memory device including a ROM and a RAM (not shown) is provided in the ultrasonic diagnostic apparatus 1. Various setting conditions for the ultrasonic diagnostic apparatus 1 and programs for controlling the ultrasonic diagnostic apparatus 1 are stored in the memory device.

(Operation)

Next, a series of operations of the ultrasonic diagnostic apparatus 1 according to the embodiment of the present invention will be described with reference to FIGS. 1A and 1B to 9. In this embodiment, a case where the ultrasonic probe 2 to be used is the one-dimensional ultrasonic probe and the ultrasonic transducers 21 are mechanically oscillated by the ultrasonic diagnostic apparatus 1 to acquire three-dimensional image data with respect to a mother and an unborn baby will be described.

In order to generate the three-dimensional image of the head of the unborn baby, the tomographic image data with respect to the mother and the unborn baby is acquired by the ultrasonic diagnostic apparatus 1. In other words, before the region of interest (ROI) is set to generate the three-dimensional image of the head of the unborn baby which is included in the set region of interest (ROI), the tomographic image data (two-dimensional information) with respect to the mother and the unborn baby is acquired by the ultrasonic diagnostic apparatus 1. For example, in the ultrasonic diagnostic apparatus 1, an ultrasound wave is transmitted from the ultrasonic probe 2 to the object to be examined (mother) without the oscillation of the ultrasonic transducers 21. Echo waves from the mother are received by the ultrasonic probe 2. The tomographic image data (two-dimensional information) with respect to the mother and the unborn baby is generated based on the received echo waves and displayed on the monitor screen of the display device 5 (Step S01).

Echo signals acquired by the ultrasonic probe 2 are outputted to the transmission and receiving device 3. The echo signals are amplified for respective receiving channels by the receiving unit of the transmission and receiving device 3 and are delayed with delay times necessary to determine the receiving directivity. The delayed echo signals are added to one another to generate the RF data. The RF data is inputted to the signal processing device 4. The B-mode ultrasonic raster data which is the two-dimensional information is generated based on the RF data by the signal processing device 4. The B-mode ultrasonic raster data which is the two-dimensional information is converted into data expressed by an orthogonal coordinate system by the signal processing device 4, thereby generating the tomographic image data (B-mode image data) as the two-dimensional information.

Figure 5A:
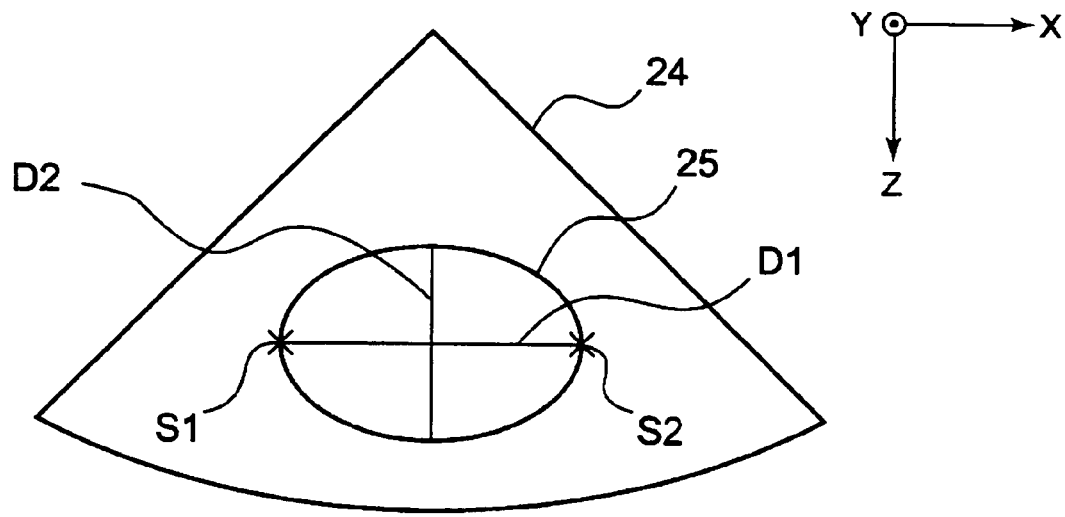
FIG. 5A shows an example of a tomographic image including a mother and an unborn baby which is displayed on a monitor screen, which shows a tomographic image of a head of the unborn baby on a scanning plane (X-Z plane)

The tomographic image data as the two-dimensional information, which is generated as described above, is outputted to the display device 5 and displayed as the tomographic image with respect to the mother and the unborn baby on the monitor screen of the display device 5. FIG. 5A shows an example of the tomographic image with respect to the mother and the unborn, which is displayed on the monitor screen of the display device 5. In order to simply explain a feature of the ultrasonic diagnostic apparatus 1 according to this embodiment, only the tomographic image of the head of the unborn baby is shown in FIG. 5A.

As shown in FIG. 5A, a tomographic image 24 with respect to the mother and the unborn, which is the two-dimensional information, is displayed on the monitor screen of the display device 5. A tomographic image 25 of the head of the unborn baby is included in the tomographic image 24. The tomographic image 25 of the head of the unborn baby is a tomographic image on the scanning plane 23 (X-Z plane). To explain it easily in FIG. 5A, the head of the unborn baby is indicated as an elliptical shape.

In order to determine the setting conditions of the region of interest (ROI) before the acquisition of the three-dimensional image data, the measurement data processing device 10 measures the development information of the unborn baby, more specifically, the size of the head of the unborn baby using the tomographic image of the head of the unborn baby as shown in FIG. 5A (Step S02).

First, in order to measure the lateral width of the head of the unborn baby (biparietal diameter), while the operator observes the tomographic image 24 displayed on the monitor screen of the display device 5, the operator operates the operation device 7 to specify both ends of the head. For example, as shown in FIG. 5A, the operator operates the operation device 7 to specify end points S1 and S2 in both ends of a head portion having a longest lateral width. When the end points S1 and S2 are specified by the operator, a length between the end point S1 and the end point S2 is measured by the measurement data processing device 10. In this embodiment, a length of a diameter of the portion having the longest lateral width, of the head (biparietal diameter) is measured by the measurement data processing device 10. Assume that the length of the diameter (biparietal diameter) is a lateral width D1.

When the lateral width D1 is obtained, a diameter of a portion having a longest longitudinal width (longitudinal width D2), of the head is calculated by the measurement data processing device 10. For example, because the head of the unborn baby can be assumed to be an ellipsoid, the head of the unborn baby is assumed to be an elliptical shape having a predetermined elliptical ratio. Therefore, the longitudinal width D2 is calculated from the elliptical ratio and the lateral width D1 by the measurement data processing device 10. The elliptical ratio is stored in the memory device (not shown), so the measurement data processing device 10 reads out the elliptical ratio from the memory device and calculates the longitudinal width D2 from the elliptical ratio and the lateral width D1. The following operation may be performed as in a case where the lateral width D1 is obtained. Points in both ends of a portion having a longest longitudinal width, of the head are specified by the operator. A length between the points is measured by the measurement data processing device 10 to set the measured length as the longitudinal width D2.

The following operation may be also performed. A circumference of the head of the unborn baby is measured by the measurement data processing device 10 without performing direct measurement on the lateral width D1 of the head of the unborn baby and the longitudinal width D2 thereof. The lateral width D1 and the longitudinal width D2 are calculated from the measured circumference by conversion. Because there is a statistical relationship between the circumference of the head and the lateral width D1 and the longitudinal width D2 of the head, when the circumference of the head is measured by the measurement data processing device 10, the lateral width and the longitudinal width can be calculated from the measured circumference by conversion. In such a case, the circumference of the head is stored in advance in the memory device (not shown) in association with the lateral width and the longitudinal width. The measurement data processing device 10 consults the memory device to obtain the lateral width and the longitudinal width which are associated with the measured circumference of the head.

Information indicating the lateral width D1 and the longitudinal width D2 which are obtained through the above-mentioned measurement is outputted from the measurement data processing device 10 to each of the control device 6 and the display device 5. Values such as the lateral width (biparietal diameter) D1 and the longitudinal width D2 are displayed on the monitor screen of the display device 5.

The measurement data processing device 10 obtains a width of the head in a depth direction thereof (width in the oscillation direction (width in the Y-direction)) based on the lateral width (biparietal diameter) D1 and outputs information indicating the width of the head in the depth direction thereof to the control device 6. Because the head of the unborn baby can be assumed to be an ellipsoid as described above, when the lateral width (biparietal diameter) D1 of the head is measured, the width in the depth direction (oscillation direction (Y-direction)) is estimated. In this embodiment, assume that the width in the depth direction (oscillation direction (Y-direction)) is D5. A shape of the head of the unborn baby and a size thereof are statistically estimated from the biparietal diameter. Therefore, a table in which the biparietal diameter is associated with the shape of the head and the size thereof is stored in advance in the memory device (not shown). The measurement data processing device 10 consults the table to obtain the width of the head in the depth direction thereof (oscillation direction (Y-direction)).

Figure 5B:
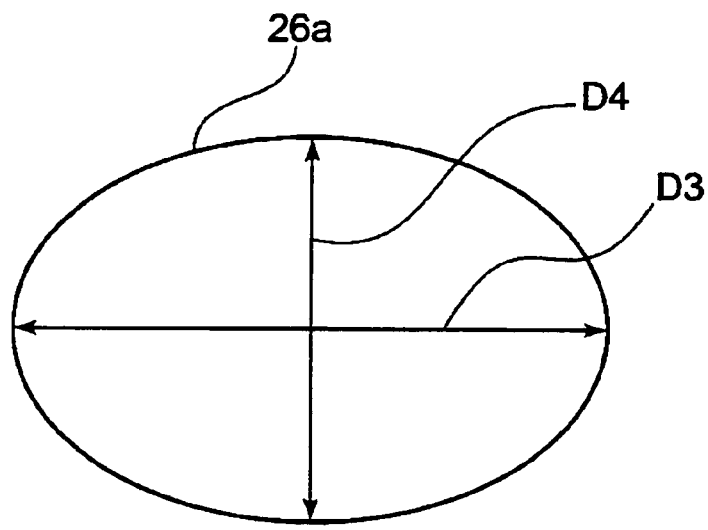
FIG. 5B shows a region of interest (ROI)

Upon receipt of the information indicating the lateral width D1 and the longitudinal width D2 from the measurement data processing device 10, the ROI width determining device 61 determines a lateral width and a longitudinal width of the region of interest (ROI) on the tomographic image data (two-dimensional information) based on the information (Step S03). For example, because the head of the unborn baby is assumed to be an ellipsoid, a shape of the region of interest (ROI) 26a is set as an elliptical shape as shown in FIG. 5B. Therefore, a lateral width D3 of the region of interest (ROI) 26a and a longitudinal width D4 thereof are determined by the ROI width determining device 61. Here, in the ROI width determining device 61, the lateral width D1 and the longitudinal width D2, each of which is multiplied by a ratio (weighting) specified by the operator, may be determined as the lateral width D3 of the elliptical region of interest (ROI) 26a and the longitudinal width D4 thereof. For example, the lateral width D3 of the region of interest (ROI) 26a and the longitudinal width D4 thereof are determined by the ROI width determining device 61 using the expression (1).

$$\text{(Lateral width } D3 \text{ of region of interest (ROI) } 26a) = \text{(lateral width } D1 \text{ of head of unborn baby)} \times \text{(ratio)} \quad \text{Expression (1)}$$

$$\text{(Longitudinal width } D4 \text{ of region of interest (ROI) } 26a) = \text{(longitudinal width } D2 \text{ of head of unborn baby)} \times \text{(ratio)}$$

The ratio in the expression (1) is a parameter specified by the operator. When the size of the head is equal to the size of the region of interest (ROI), "standard" is set. Assume that "standard" indicates 100%. In the case of "standard" (100%), the lateral width D3 of the region of interest (ROI) 26a and the longitudinal width D4 thereof are determined by the ROI width determining device 61 with a condition in which the ratio is equal to "1". In this case, the lateral width D3 of the region of interest (ROI) becomes equal to the lateral width D1 of the head and the longitudinal width D4 of the region of interest (ROI) becomes equal to the longitudinal width D2 of the head.

The size of the region of interest (ROI) to the size of the head can be adjusted according to the ratio selected by the operator using the operation device 7. For example, when 110% is selected as "standard", the lateral width D3 of the region of interest (ROI) and the longitudinal width D4 thereof are determined by the ROI width determining device 61 with a condition in which the ratio is equal to "1.1". In this case, the lateral width D3 of the region of interest (ROI) becomes "1.1 times" the lateral width D1 of the head and the longitudinal width D4 of the region of interest (ROI) becomes "1.1 times" the longitudinal width D2 of the head.

Such a ratio can be arbitrarily selected. For example, "standard" (100%), 90% of "standard", 110% of "standard", 120% of "standard", 130% of "standard", or the like can be selected. When the ratio is inputted from the operation device 7 by the operator, the lateral width D3 of the region of interest (ROI) and the longitudinal width D4 thereof are determined based on the inputted ratio by the ROI width determining device 61.

As described above, the lateral width D3 and the longitudinal width D4 of the region of interest (ROI) 26a on the tomographic image data (two-dimensional information) are determined by the ROI width determining device 61. The region of interest (ROI) 26a is a region of interest on the tomographic image data acquired when the ultrasonic transducers 21 are not oscillated. In other words, the region of interest (ROI) 26a corresponds to a region of interest on the tomographic image data acquired when the oscillation angle θ shown in FIG. 2B is "0°".

The last menstrual date of the mother which is included in the patient information of the mother may be used for another method of determining the lateral width of the region of interest (ROI) and the longitudinal width thereof. In such a case, first, the patient information including the last menstrual date of the mother is inputted from the operation device 7 to the ultrasonic diagnostic apparatus 1 by the operator. The patient data processing device 11 receives the patient information through the control device 6 and calculates the unborn baby age from the last menstrual date. Because there is a statistical relationship between the unborn baby age and the size of the unborn baby, the patient data processing device 11 determines the size of the head of the unborn baby based on the unborn baby age. For example, a table in which the unborn baby age is associated with the size of the head of the unborn baby is stored in advance in the memory device (not shown). The patient data processing device 11 consults the table to obtain the size (lateral width D1, longitudinal width D2, and width D5 in a depth direction) of the head of the unborn baby based on unborn baby age. The information indicating the lateral width D1 of the head and the longitudinal width D2 thereof which are thus obtained is outputted to the ROI width determining device 61 of the control device 6. As in the operation described above, the lateral width D3 of the region of interest (ROI) 26a and the longitudinal width D4 thereof are determined by the ROI width determining device 61.

As described above, when the lateral width D3 and the longitudinal width D4 of the region of interest (ROI) 26a on the tomographic image data acquired at the oscillation angle θ of "0°" are determined, the range of the oscillation angle θ is then determined by the oscillation angle determining device 62 (Step S04). A method of determining the range of the oscillation angle θ will be described with reference to FIG. 6.

First, the operator specifies a position of the region of interest (ROI) 26a to be displayed on the monitor screen of the display device 5. For example, while the operator observes the tomographic image 24 displayed on the monitor screen of the display device 5, the operator operates the operation device 7 to specify the position of the region of interest (ROI) 26a including the head of the unborn baby, which is to be displayed thereon. The specified position corresponds to an upper end portion of the region of interest (ROI) 26a.

The oscillation angle determining device 62 determines the range of the oscillation angle θ based on a distance between the oscillation center point 21a and the surface of the ultrasonic probe 2, the specified position of the region of interest (ROI) 26a to be displayed, the longitudinal width D4 of the region of interest (ROI) 26a, and the shape (in the depth direction (width D5 in an oscillation direction)) of the head of the unborn baby.

Figure 6:
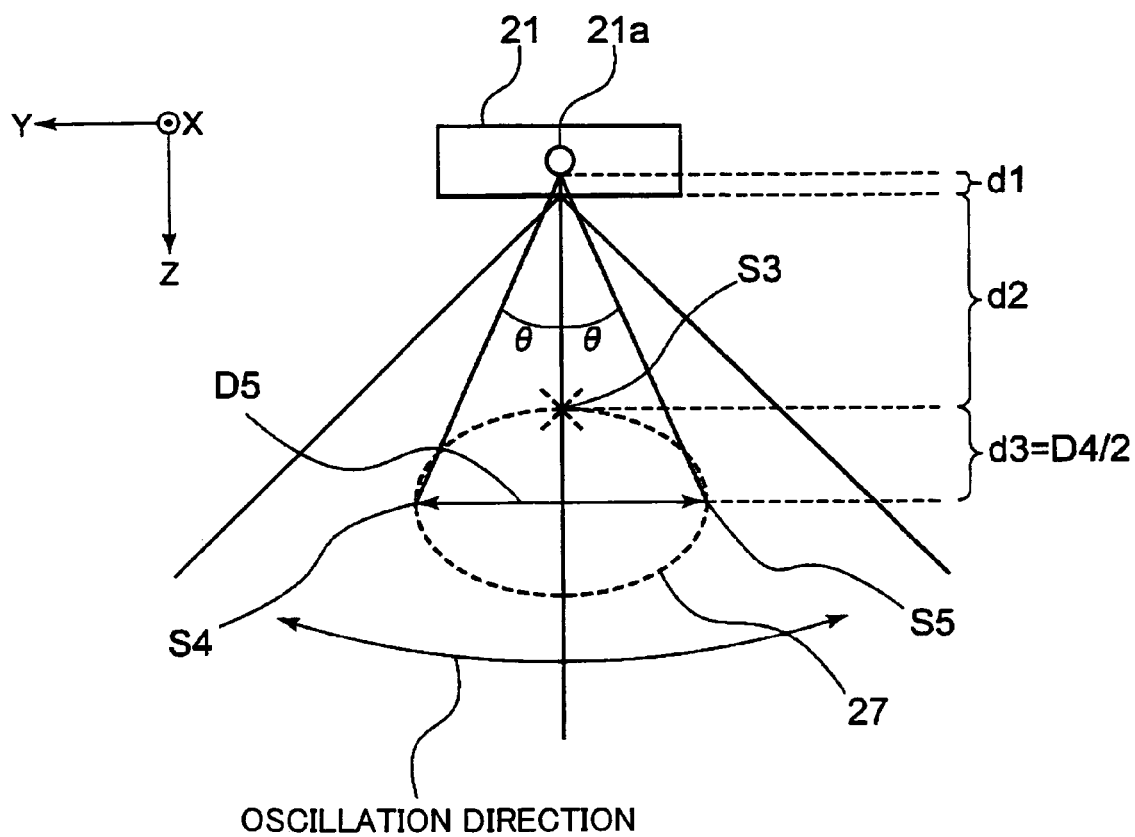
FIG. 6 is an explanatory view for an operation for obtaining an angle for oscillating the ultrasonic transducers, which is a side view showing the ultrasonic transducers.

As shown in FIG. 6, the distance between the oscillation center point 21a of the ultrasonic transducers 21 and the surface of the ultrasonic probe 2 is expressed as a distance d1. The position of the region of interest (ROI) 26a to be displayed, which is specified by the operator, is expressed as a specified position S3. A distance between the surface of the ultrasonic probe 2 and the specified position S3 of the region of interest (ROI) 26a is expressed as a distance d2. Assume that a half value of the longitudinal width D4 of the region of interest (ROI) 26a is d3 (=D4/2). The shape of the head, more specifically, the width D5 of the head in the depth direction (oscillation direction (Y-direction)) is obtained by the measurement data processing device 10. Note that FIG. 6 shows a shape of a head 27 of the unborn baby in the depth direction (oscillation direction (Y-direction)). To explain it easily in FIG. 6, the shape of the head in the depth direction (oscillation direction (Y-direction)) is indicated as an elliptical shape.

The oscillation angle determining device 62 obtains the oscillation angle θ based on the above-mentioned parameters. In order to obtain the oscillation angle θ, first, the oscillation angle determining device 62 calculates a sum of the distance d1 between the oscillation center point 21a and the surface of the ultrasonic probe 2, the distance d2 between the surface of the ultrasonic probe 2 and the specified position S3 of the region of interest (ROI) 26a, and the half value d3 of the longitudinal width D4. In other words, the oscillation angle determining device 62 calculates (d1+d2+d3). Assume that a half value of the width D5 in the depth direction (oscillation direction (Y-direction)) is d4 (=D5/2). The oscillation angle determining device 62 determines the range of the oscillation angle θ using the under-mentioned expression (2).

$$\text{Oscillation angle } \theta = \tan^{-1}\{d4/(d1+d2+d3)\} \quad \text{Expression (2)}$$

When the ultrasonic transducers 21 are oscillated within the oscillation angle θ expressed by the expression (2), a tomographic image including both end points S4 and S5 of the head 27 in the depth direction (oscillation direction (Y-direction)) and vicinities thereof is acquired.

The oscillation angle θ may be multiplied by the above-mentioned ratio. For example, when "standard" is specified by the operator, the oscillation angle determining device 62 multiplies the angle calculated by the expression (2) by the ratio of "1" to obtain the oscillation angle. When 110% of "standard" is specified, the oscillation angle determining device 62 multiplies the angle calculated by the expression (2) by the ratio of "1.1" to obtain the oscillation angle.

As described above, according to the ultrasonic diagnostic apparatus 1 according to this embodiment, the oscillation angle is calculated based on the unborn baby development information, that is, the size (lateral width, longitudinal width, and width in a depth direction) of the head of the unborn baby. Therefore, the ultrasonic transducers 21 can be oscillated for scanning within the scanning region based on the shape of the head of the unborn baby, with the result that the image in a region corresponding to the size of the head of the unborn baby can be acquired.

When the oscillation angle θ is determined, the information indicating the range of the determined oscillation angle is outputted to the probe oscillation control device 8. After the oscillation angle is determined, the size of the region of interest (ROI) which is associated with each oscillation angle is determined by the ROI width determining device 61 (Step S05). The operation for obtaining the size of the region of interest (ROI) associated with the oscillation angle will be described with reference to FIGS. 7A and 7B.

Figure 7A:
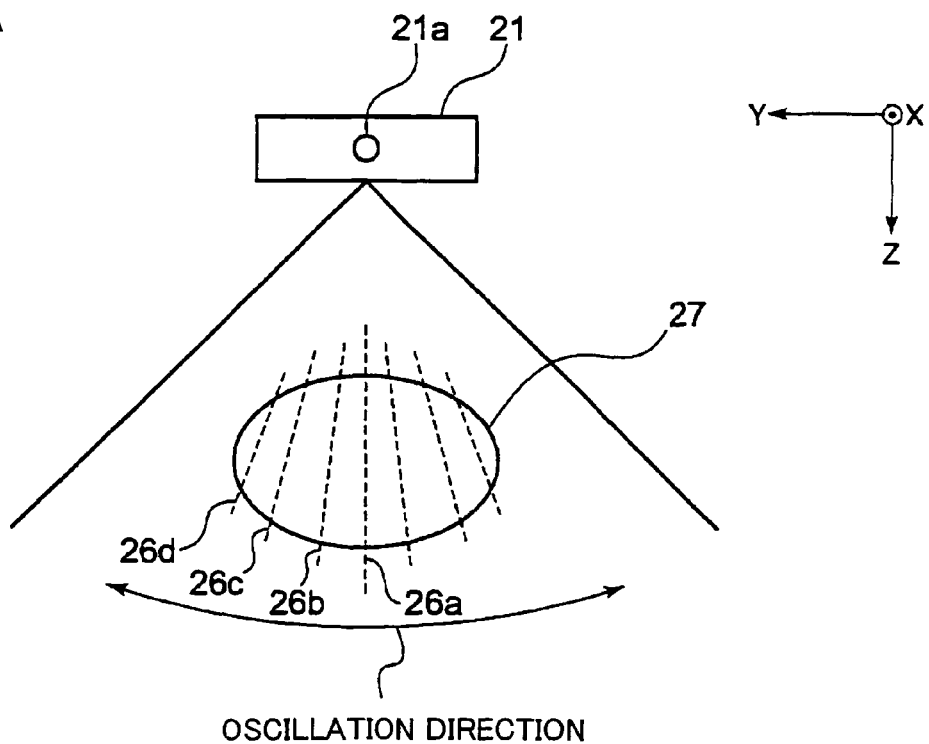
FIG. 7A is an explanatory view for an operation for obtaining a size of the region of interest (ROI) which is associated with the angle for oscillating the ultrasonic transducers, which is a side view showing the ultrasonic transducers.

As shown in FIG. 7A, the head of the unborn baby can be assumed to be an ellipsoid. A cross sectional area of the head at the oscillation angle of "0°" is large and the cross sectional area becomes gradually smaller as the oscillation angle increases. Therefore, when the oscillation angle increases, the lateral width D3 of the region of interest (ROI) and the longitudinal width D4 thereof are shortened by the ROI width determining device 61. The shape of the head of the unborn baby and the size thereof are statistically found, so the shape of the head of the unborn baby and the size thereof are stored in advance in the memory device (not shown) as described above. The ROI width determining device 61 obtains the lateral width of the region of interest (ROI) and the longitudinal width thereof which are associated with each oscillation angle based on the shape of the head of the unborn baby and the size thereof which are stored in the memory device, the lateral width D3 of the region of interest (ROI) 26a and the longitudinal width D4 thereof, and the range of the oscillation angle.

For example, in the ROI width determining device 61, when the oscillation angle is "0°", the region of interest (ROI) 26a is assumed. When the oscillation angle is "10° and −10°", the region of interest (ROI) 26b is assumed. When the oscillation angle is "20° and −20°", the region of interest (ROI) 26c is assumed. When the oscillation angle is "30° and −30°", the region of interest (ROI) 26d is assumed.

Figure 7B:
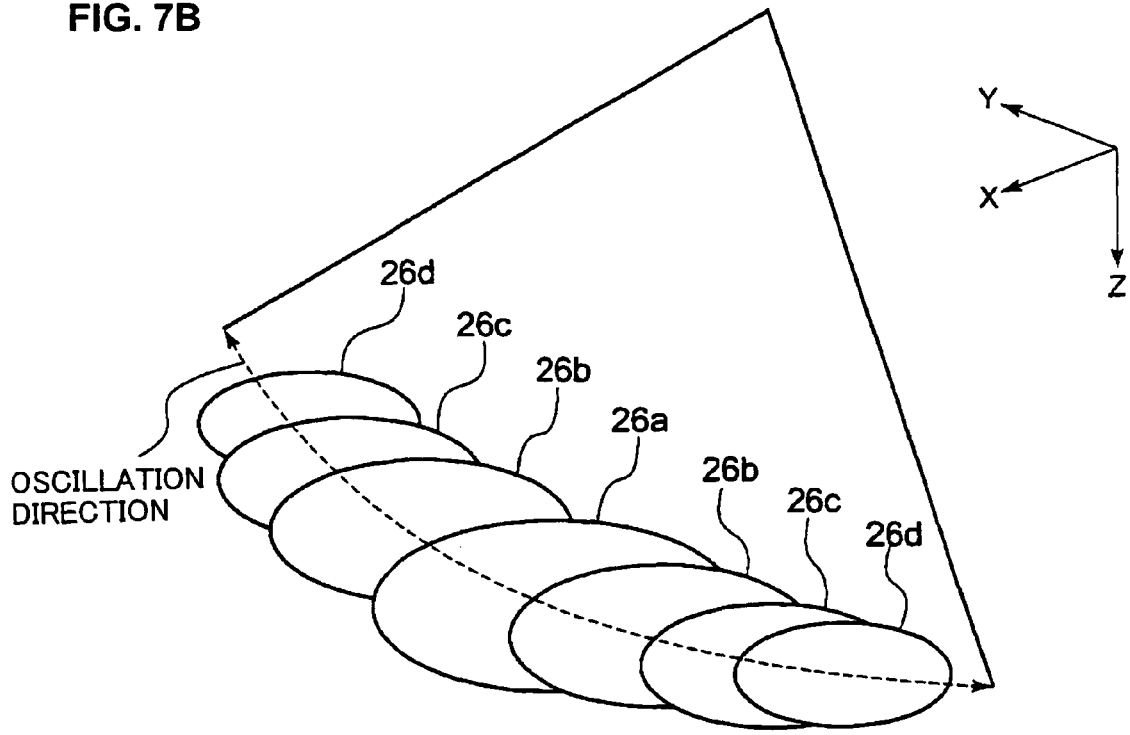
FIG. 7B is a schematic explanatory view for the operation for obtaining the size of the region of interest (ROI) which is associated with the angle for oscillating the ultrasonic transducers.

As shown in FIGS. 7A and 7B, the region of interest (ROI) 26a associated with the oscillation angle of "0°" has a longest lateral width and a longest longitudinal width, so that it has a largest size. The lateral width and the longitudinal width of the region of interest (ROI) 26b which are associated with the oscillation angle of "10°, −10°" become shorter than those of the region of interest (ROI) 26a. The lateral width and the longitudinal width of the region of interest (ROI) 26c which are associated with the oscillation angle of "20°, −20°" become shorter than those of the region of interest (ROI) 26b. The lateral width and the longitudinal width of the region of interest (ROI) 26d which are associated with the oscillation angle of "30°, −30°" become shorter than those of the region of interest (ROI) 26c. Therefore, when the region of interest (ROI) which is to be set becomes closer to the end portion of the head 27 of the unborn baby, the lateral width and the longitudinal width of the set region of interest (ROI) are shortened by the ROI width determining device 61, thereby decreasing the size of the region of interest.

As described above, in the ultrasonic diagnostic apparatus 1, when the lateral width and the longitudinal width (size) of the region of interest (ROI) are adjusted according to the oscillation angle, it is possible to set the region of interest (ROI) corresponding to the shape of the head of the unborn baby. Therefore, the three-dimensional image of the head of the unborn baby can be preferably extracted and displayed.

The information indicating the region of interest (ROI) is outputted from the control device 6 to the three-dimensional processing device 9.

When the range of the oscillation angle is determined, the rate (oscillation rate) for oscillating the ultrasonic transducers 21 is determined by the oscillation rate determining device 63 (Step S06). The operation for determining the oscillation rate will be described with reference to FIG. 8.

A table of FIG. 8 shows information stored in advance in a memory device (not shown) of the ultrasonic diagnostic apparatus 1. This table includes the range of the oscillation angle for oscillating the ultrasonic transducers 21, the information indicating image quality, and the oscillation rate, which are associated with one another. The range of the oscillation angle is obtained by the oscillation angle determining device 62. The information indicating image quality is determined by the selection of the operator and corresponds to information inputted from the operation device 7.

Upon receipt of the information indicating the range of the oscillation angle and image quality, the oscillation rate determining device 63 consults the table shown in FIG. 8 to determine the rate (oscillation rate) for oscillating the ultrasonic transducers 21. For example, assume that the maximum range of the oscillation angle is "45°, −45°". In such a case, when "high quality" is selected by the operator, the oscillation rate determining device 63 selects the rate of "90" from the table. When "intermediate quality" is selected, the rate of "110" is selected. When "low quality" is selected, the rate of "130" is selected. Therefore, the oscillation rate increases as the image quality is shifted from the high quality to the low quality. In other words, when a high quality image is to be acquired, the ultrasonic diagnostic apparatus 1 performs scanning with a state in which the oscillation rate of the ultrasonic transducers 21 is low. On the other hand, when the priority of the scanning speed is to be made higher than that of the image quality, the scanning is performed with a state in which the oscillation rate of the ultrasonic transducers 21 is high.

The oscillation rate is related to an ultrasonic scanning line density. In other words, the ultrasonic scanning line density becomes less dense as the oscillation rate increases. The ultrasonic scanning line density becomes denser as the oscillation rate decreases. Because the ultrasonic scanning line density becomes less dense as the oscillation rate increases, the quality of an acquired ultrasonic image is changed from high quality to low quality. However, the scanning speed increases as the oscillation rate increases, so the real time operation of the ultrasonic diagnostic apparatus 1 can be improved. On the other hand, because the ultrasonic scanning line density becomes denser as the oscillation rate decreases, the quality of an acquired ultrasonic image is changed from low quality to high quality.

As described above, a relative relationship is held between the quality (scanning line density) of the ultrasonic image and the ultrasonic scanning speed. When "high quality" is selected by the operator, a high quality ultrasonic image can be obtained. When "low quality" is selected to acquire an image such as a blood flow image, a frame rate can be increased, so that the image can be obtained with an improved realtimeness.

Thus, when the oscillation rate of the ultrasonic transducers 21 is determined by the oscillation rate determining device 63, the information indicating the oscillation rate thereof is outputted to the probe oscillation control device 8.

The probe oscillation control device 8 controls the oscillation of the ultrasonic transducers 21 based on the information indicating the oscillation angle and the information indicating the oscillation speed which are outputted from the control device 6. When the oscillation control of the ultrasonic transducers 21 is performed by the probe oscillation control device 8 and the ultrasonic transmission and receiving control is performed by the transmission and receiving device 3, an echo signal is acquired at each oscillation angle by the ultrasonic probe 2. The echo signal acquired at each oscillation angle is outputted to the signal processing device 4. The signal processing device 4 generates tomographic data associated with each oscillation angle based on the echo signal and outputs the tomographic data associated with each oscillation angle to the three-dimensional image processing device 9 (Step S07).

The three-dimensional image processing device 9 reconstructs three-dimensional image data from the tomographic image data associated with each oscillation angle using a known method. At the time of reconstruction, the information indicating the size (lateral width and longitudinal width) of the region of interest (ROI) which is associated with each oscillation angle is outputted from the control device 6 to the three-dimensional image processing device 9. Therefore, the three-dimensional image processing device 9 extracts, from the tomographic image data associated with each oscillation angle, image data included in the region of interest (ROI) which is associated with a corresponding oscillation angle (Step S08). For example, the region of interest (ROI) 26a is associated with the oscillation angle of "0°", so the three-dimensional image processing device 9 extracts the image data included in the region of interest (ROI) 26a associated therewith from the tomographic image data acquired at the oscillation angle of "0°". With respect to another oscillation angle, the same operation is performed. For example, the region of interest (ROI) 26b is associated with the oscillation angle of "10°, −10°", so the three-dimensional image processing device 9 extracts the image data included in the region of interest (ROI) 26b associated therewith from the tomographic image data acquired at the oscillation angle of "10°, −10°". Then, the three-dimensional image processing device 9 reconstructs the three-dimensional image data from the extracted tomographic image data associated with each oscillation angle. The reconstructed three-dimensional image data is outputted to the display device 5, so that the three-dimensional image of the head of the unborn baby is displayed on the display device 5.

As described above, according to the ultrasonic diagnostic apparatus 1 according to this embodiment, when the size (lateral width and longitudinal width) of the region of interest (ROI), the oscillation angle, the oscillation rate, and the size of the region of interest (ROI) associated with each oscillation angle are obtained from the size (lateral width, longitudinal width, and width in a depth direction) of the head of the unborn baby, it is possible to reconstruct the three-dimensional data based on the shape of the head of the unborn baby. Therefore, the ultrasonic diagnostic apparatus 1 can suitably extract and display the three-dimensional image of the head of the unborn baby.

Up to now, the size of the region of interest (ROI), the oscillation angle, and the oscillation rate are determined by the operator on experience or intuition. According to the ultrasonic diagnostic apparatus 1 according to this embodiment, when the unborn baby development information or the unborn baby age information is obtained, the size of the region of interest (ROI), the oscillation angle, and the oscillation rate which are suitable to extract the three-dimensional image of the head of the unborn baby are automatically determined. Therefore, the setting of the region of interest which is performed by the operator can be omitted.

When the three-dimensional image of the head of the unborn baby is not suitably extracted using the size of the region of interest (ROI), the oscillation angle, and the oscillation rate which are determined by the above-mentioned operation, it is necessary to reset the size of the region of interest, the oscillation angle, and the oscillation rate to perform scanning again. Even when such resetting is necessary, the frequency of the resetting can be reduced by using the ultrasonic diagnostic apparatus 1 according to this embodiment. In other words, even when the parameters such as the size of the region of interest and the oscillation angle which are set to suitably extract the three-dimensional image of the head of the unborn baby are outside an optimum condition, such deviation from the optimum condition may be slight because the size of the region of interest, the oscillation angle, and the like which are suitable for the shape of the head of the unborn baby are obtained by the ROI width determining device 61 and the like. Because the parameters are slightly deviated from the optimum condition, the frequency of the resetting performed by the operator can be reduced. Further in a case of resetting, it is only necessary to change the above-mentioned ratio to a suitable ratio by the operator, with the result that the size of the region of interest, the oscillation angle, and the like which are suitable to extract the three-dimensional image of the head of the unborn baby are obtained. Therefore, even when suitable setting conditions of the region of interest are not obtained in first setting, the frequency of the resetting performed by the operator can be reduced. As a result, an examination time can be shortened to reduce burdens on a patient and the operator.

Figure 9A:
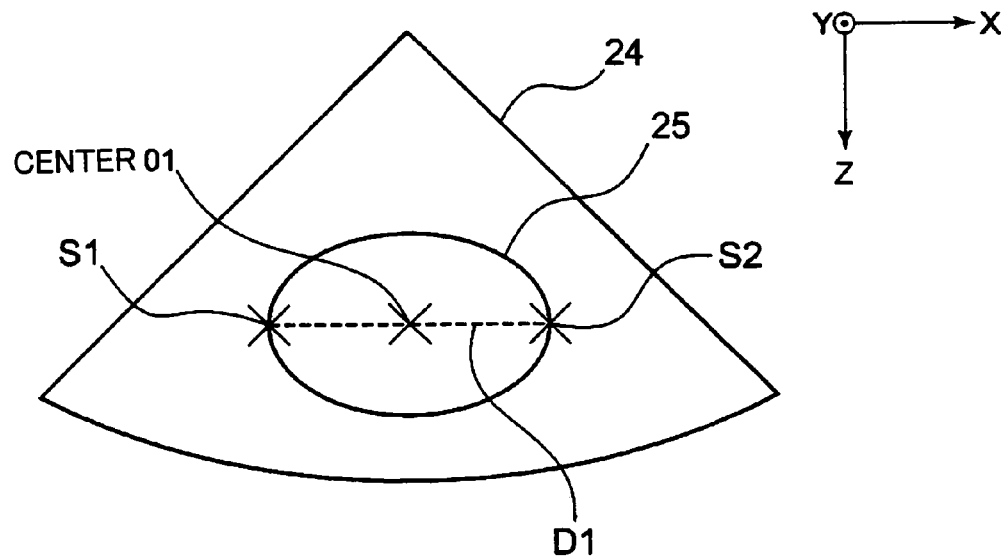
FIG. 9A is an explanatory view for an operation for obtaining a center position of the region of interest (ROI), which shows a tomographic image of the head of the unborn baby on the scanning plane (X-Z plane)
Figure 9B:
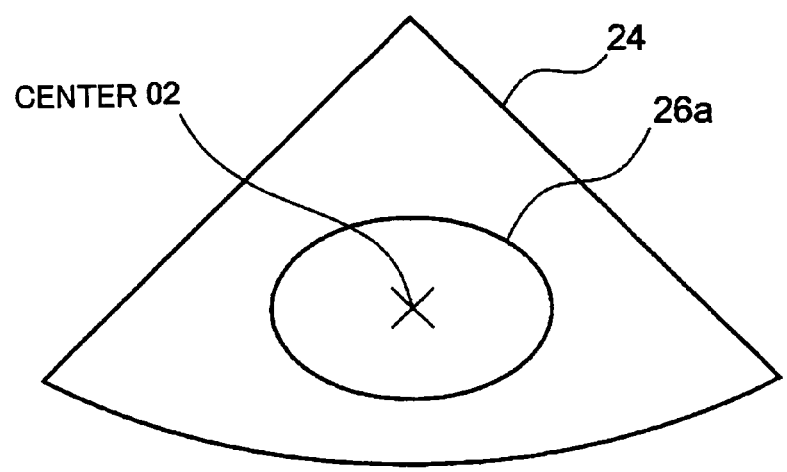
FIG. 9B shows the region of interest (ROI)

According to the ultrasonic diagnostic apparatus 1 according to this embodiment, the position of the region of interest (ROI) can be automatically determined. Such an operation will be described with reference to FIGS. 9A and 9B. When the end points S1 and S2 are specified as shown in FIG. 9A by the operator to measure the lateral width of the head of the unborn baby (biparietal diameter) in Step S02, the ROI position determining device 64 obtains a position (coordinates) of a center point O1 of the lateral width D1 from the positions (coordinates) of the end points S1 and S2. Then, the ROI position determining device 64 determines a position (coordinates) of a center point O2 of the region of interest (ROI) 26a shown in FIG. 9B based on the position (coordinates) of the center point O1 using the under-mentioned expression (3).

Position (coordinates) of center point $O2$ of region of interest (ROI) $26a$ =(Position (coordinates) of center point $O1$)×(ratio)   Expression (3)

As described above, the ratio is the parameter arbitrarily determined by the operator and "standard" is assumed to be 100%. It is possible to select 110% of "standard", 120% of "standard", or the like. For example, when "standard" is selected by the operator, the ratio becomes "1.0", so that the position (coordinates) of the center point O2 of the region of interest (ROI) 26a coincides with the center point O1 (coordinates). When 110% of "standard" is selected, the ratio becomes "1.1". In this case, the ROI position determining device 64 multiplies the coordinates of the region of interest (ROI) 26a in the Z-direction (depth direction) by "1.1".

Therefore, according to the ultrasonic diagnostic apparatus 1 according to this embodiment, the position (coordinates) of the region of interest (ROI) 26a on the X-Z plane can be automatically determined based on the end points S1 and S2 specified to measure the lateral width of the head of the unborn baby (biparietal diameter).

Next, an example with respect to another diagnostic region will be described. In the above-mentioned example, a region including the mother and the unborn baby is set as a target region for image taking. Even when a region other than target region including the mother and the unborn baby is subjected to image taking, a three-dimensional image based on the shape of such region is obtained by the ultrasonic diagnostic apparatus 1. Hereinafter, an example in which a three-dimensional image of a tumor which is the target region for image taking is displayed will be described.

Assume that the target region for image taking is a tumor of a thyroid. In order to generate three-dimensional image data of the tumor, tomographic image data of the tumor caused in the thyroid is acquired by the ultrasonic diagnostic apparatus 1. In the ultrasonic diagnostic apparatus 1, an ultrasonic wave is transmitted from the ultrasonic probe 2 to the object to be examined (thyroid) without the oscillation of the ultrasonic transducers 2. Echo waves from the object to be examined are received by the ultrasonic probe 2. The tomographic image data of a region including the tumor is generated based on the received echo waves and displayed on the monitor screen of the display device 5.

Figure 10:
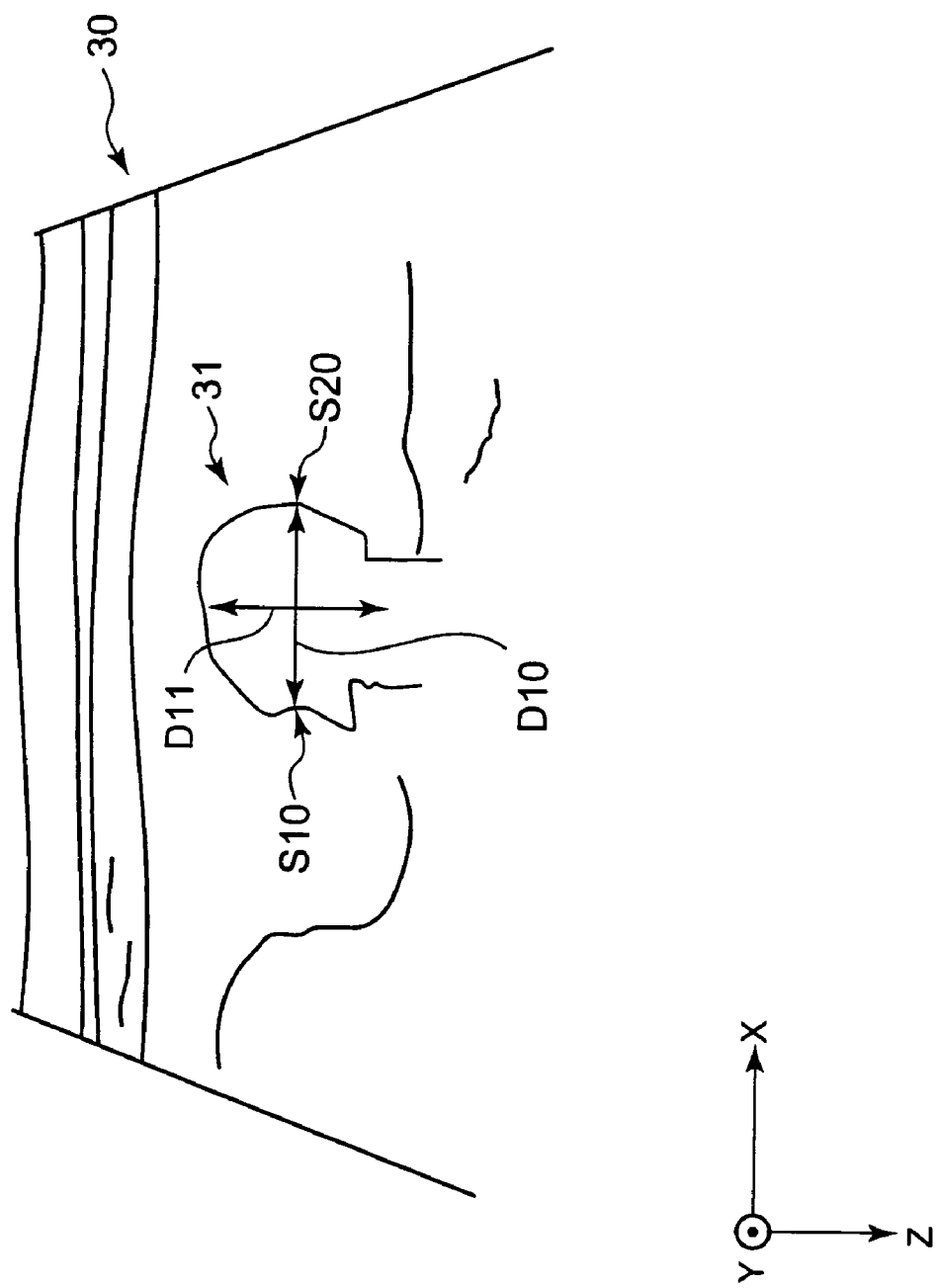
FIG. 10 shows an example of a tomographic image of a tumor which is displayed on the monitor screen, which shows the tomographic image of the tumor on the scanning plane (X-Z plane).

The tomographic image data as the two-dimensional information, which is generated as described above, is outputted to the display device 5 and displayed as a tomographic image of the region including the tumor on the monitor screen of the display device 5. FIG. 10 shows an example of the tomographic image of the region including the tumor, which is displayed on the monitor screen of the display device 5.

As shown in FIG. 10, a tomographic image 30 of the region including the tumor is displayed as the two-dimensional information on the monitor screen of the display device 5. A tomographic image 31 of the tumor is included in the tomographic image 30. The tomographic image 31 of the tumor is a tomographic image on the scanning plane 23 (X-Z plane).

In order to determine the setting conditions of the region of interest (ROI) before the acquisition of the three-dimensional image data, the measurement data processing device 10 measures the size of the tumor using the tomographic image 31 of the tumor as shown in FIG. 10.

First, in order to measure the lateral width of the tumor, while the operator observes the tomographic image 30 displayed on the monitor screen of the display device 5, the operator operates the operation device 7 to specify both ends of the tumor. For example, as shown in FIG. 10, when end points S10 and S20 located in both ends of a tumor portion having a longest lateral width are specified by the operator, a length between the end point S10 and the end point S20 is measured by the measurement data processing device 10. In this case, a length of the portion having the longest lateral width, of the tumor is measured by the measurement data processing device 10. Assume that the length of the portion having the longest lateral width is a lateral width D10.

When the lateral width D10 is obtained, a length of a portion having a longest longitudinal width, of the tumor (longitudinal width D11) is calculated by the measurement data processing device 10. As in the case where the lateral width D10 is obtained, both end points of the portion having the longest longitudinal width, of the tumor are specified by the operator and a length between the points is measured by the measurement data processing device 10 to set the measured length as the longitudinal width D11.

The following operation may be performed identically as in the example with respect to the mother and the unborn baby. A circumference of the tumor is measured by the measurement data processing device 10 without performing direct measurement on the lateral width D10 of the tumor and the longitudinal width D11 thereof. The lateral width D10 and the longitudinal width D11 are calculated from the measured circumference by conversion.

The lateral width D10 and the longitudinal width D11 which are obtained through the above-mentioned measurement are outputted from the measurement data processing device 10 to each of the control device 6 and the display device 5. Obtained values such as the lateral width D10 and the longitudinal width D11 are displayed on the monitor screen of the display device 5.

The measurement data processing device 10 obtains a width of the tumor in a depth direction thereof (width in the oscillation direction (width in the Y-direction)) based on the lateral width D10 (or longitudinal width D11) and outputs information indicating the width of the tumor in the depth direction thereof to the control device 6. Assume that the width in the depth direction (oscillation direction (Y-direction)) is D12. A shape of the tumor and a size thereof are statistically estimated from the lateral width D10 (or longitudinal width D11). Therefore, a table in which the lateral width D10 (or longitudinal width D11) is associated with the shape of the tumor and the size thereof is stored in advance in the memory device (not shown). The measurement data processing device 10 consults the table to obtain the width D12 of the tumor in the depth direction (oscillation direction (Y-direction)).

Upon receipt of the information indicating the lateral width D10 and the longitudinal width D11 from the measurement data processing device 10, the ROI width determining device 61 determines the lateral width and the longitudinal width of the region of interest (ROI) on the tomographic image (two-dimensional information) based on the received information. As in the example with respect to the mother and the unborn baby, the tumor which is the diagnostic region is assumed to be an ellipsoid, so the shape of the region of interest (ROI) 26a is set as the elliptical shape as shown in FIG. 5B. Therefore, the lateral width D3 of the region of interest (ROI) 26a and the longitudinal width D4 thereof are determined by the ROI width determining device 61. As in the above-mentioned embodiment, in the ROI width determining device 61, the lateral width D10 and the longitudinal width D11, each of which is multiplied by the ratio (weighting) specified by the operator, may be determined as the lateral width D3 of the elliptical region of interest (ROI) 26a and the longitudinal width D4 thereof. For example, as in the above-mentioned embodiment, the lateral width D3 of the region of interest (ROI) 26a and the longitudinal width D4 thereof are determined by the ROI width determining device 61 using the expression (1).

In some cases, a doctor observes the tumor and blood vessels located around the tumor to conduct diagnosis. In such cases, it is necessary to display an ultrasonic image including the tumor and the blood vessels located around the tumor on the display device 5. Therefore, the ratio in the expression (1) increases to increase the size of the region of interest (ROI). For example, when 110% of "standard" is selected by the operator so as to include the blood vessels located around the tumor in the ultrasonic image, the lateral width D3 of the region of interest (ROI) 26a and the longitudinal width D4 thereof are determined by the ROI width determining device 61 with a condition in which the ratio is equal to "1.1". In this case, the lateral width D3 of the region of interest (ROI) becomes "1.1 times" the lateral width D10 of the tumor and the longitudinal width D4 of the region of interest (ROI) also becomes "1.1 times" the longitudinal width D11 of the tumor. As in the above-mentioned embodiment, the ratio can be arbitrarily selected by the operator. The ratio is changed to 120% or 130% by the operator so as to include the blood vessels located around the tumor in the ultrasonic image.

As described above, the lateral width D3 and the longitudinal width D4 of the region of interest (ROI) 26a on the tomographic image data (two-dimensional information) are determined by the ROI width determining device 61. The region of interest (ROI) 26a is a region of interest on the tomographic image data acquired when the ultrasonic transducers 21 are not oscillated.

As described above, after the lateral width D3 and the longitudinal width D4 of the region of interest (ROI) 26a on the tomographic image data acquired at the oscillation angle θ of "0°" are determined, the range of the oscillation angle θ is determined by the oscillation angle determining device 62.

As in the example with respect to the mother and the unborn baby, for example, while the operator observes the tomographic image 30 displayed on the monitor screen of the display device 5, the operator operates the operation device 7 to specify the position of the region of interest (ROI) 26a including the tumor, which is to be displayed thereon. The specified position corresponds to an upper end portion of the region of interest (ROI) 26a.

The oscillation angle determining device 62 determines the range of the oscillation angle θ based on a distance between the oscillation center point 21a and the surface of the ultrasonic probe 2, the specified position of the region of interest (ROI) 26a to be displayed, the longitudinal width D4 of the region of interest (ROI) 26a, and the shape (width D5 in the depth direction (oscillation direction)) of the tumor.

A specific method of determining the range of the oscillation angle θ is identical to the method with respect to the mother and the unborn baby. The oscillation angle determining device 62 determines the oscillation angle θ using the above-mentioned expression (2). When the ultrasonic transducers 21 are oscillated within the oscillation angle θ determined using the expression (2), a tomographic image including the ends of the tumor in the depth direction and vicinities thereof is acquired.

The oscillation angle θ may be multiplied by the above-mentioned ratio. For example, when the tumor and the blood vessels located around the tumor are to be observed to conduct diagnosis, the angle obtained using the expression (2) may be increased to widen the range in which the ultrasonic transducers 21 are oscillated. For example, when 110% of "standard" with respect to the oscillation angle is selected by the operator so as to include the blood vessels located around the tumor in the ultrasonic image, the oscillation angle θ is calculated by the oscillation angle determining device 62 with a condition in which the ratio is equal to "1.1". As in the example with respect to the mother and the unborn baby, the ratio can be arbitrarily selected by the operator. The ratio is changed to 120% or 130% by the operator so as to include the blood vessels located around the tumor in the ultrasonic image.

As described above, when the oscillation angle θ is determined, the information indicating the range of the determined oscillation angle is outputted to the probe oscillation control device 8. After the oscillation angle is determined, the size of the region of interest (ROI) which is associated with each oscillation angle is determined by the ROI width determining device 61. For example, when the tumor is assumed to be an ellipsoid, a cross sectional area of the tumor at the oscillation angle of "0°" is large and the cross sectional area of the tumor becomes gradually smaller as the oscillation angle increases. Therefore, as the oscillation angle increases, the lateral width D3 of the region of interest (ROI) and the longitudinal width D4 thereof are shortened by the ROI width determining device 61. The shape of the tumor of the unborn baby and the size thereof are stored in advance in the memory device (not shown). The ROI width determining device 61 obtains the lateral width of the region of interest (ROI) and the longitudinal width thereof which are associated with each oscillation angle based on the shape of the tumor and the size thereof which are stored in the memory device, the lateral width D3 of the region of interest (ROI) 26a and the longitudinal width D4 thereof, and the range of the oscillation angle.

For example, as shown in FIG. 7B, in the ROI width determining device 61, the lateral width of the region of interest (ROI) and the longitudinal width thereof are shortened as the oscillation angle increases. In addition, as the region of interest (ROI) becomes closer to the end portion of the tumor, the lateral width and the longitudinal width of the region of interest are shortened to decrease the size of the region of interest.

As described above, in the ultrasonic diagnostic apparatus 1, when the lateral width and the longitudinal width (size) of the region of interest (ROI) are adjusted according to the oscillation angle, it is possible to set the region of interest (ROI) suitable for the shape of the tumor. Therefore, the three-dimensional image of the tumor can be preferably extracted and displayed. The information indicating the region of interest (ROI) is outputted from the control device 6 to the three-dimensional processing device 9.

When the range of the oscillation angle is determined, as in the example with respect to the mother and the unborn baby, the oscillation rate determining device 63 consults the table shown in FIG. 8 to determine the oscillation rate of the ultrasonic transducers 21. Upon receipt of the information indicating the range of the oscillation angle which is determined by the oscillation angle determining device 62 and the information indicating image quality which is selected by the operator, the oscillation rate determining device 63 consults the table shown in FIG. 8 to determine the oscillation rate of ultrasonic transducers 21. When a high quality image is to be acquired, scanning is performed with a low oscillation rate of the ultrasonic transducers 21. On the other hand, when the priority of the scanning speed is to be made higher than that of the image quality, the scanning is performed with a high oscillation rate of the ultrasonic transducers 21.

For example, when image display is performed by color flow mapping (CFM) to allow observation of the blood flow of the blood vessels located around the tumor, it is necessary to increase the scanning speed to the extent in which the blood flow can be observed. In such a case, when "intermediate quality" or "high quality" is selected by the operator, the frame rate can be increased, so that the image can be obtained with an improved realtimeness.

Thus, when the oscillation rate of the ultrasonic transducers 21 is determined by the oscillation rate determining device 63, the information indicating the oscillation rate thereof is outputted to the probe oscillation control device 8.

The probe oscillation control device 8 controls the oscillation of the ultrasonic transducers 21 based on the information indicating the oscillation angle and the information indicating the oscillation rate which are outputted from the control device 6. When the oscillation control of the ultrasonic transducers 21 is performed by the probe oscillation control device 8 and the ultrasonic transmission and receiving control is performed by the transmission and receiving device 3, an echo signal is acquired at each oscillation angle. The signal processing device 4 generates tomographic image data associated with each oscillation angle based on the echo signal and outputs the tomographic image data to the three-dimensional image processing device 9.

The three-dimensional image processing device 9 reconstructs three-dimensional image data from the tomographic image data associated with each oscillation angle. At the time of reconstruction, the three-dimensional image processing device 9 extracts, from the tomographic image data associated with each oscillation angle, image data included in the region of interest (ROI) which is associated with a corresponding oscillation angle. Then, the three-dimensional image processing device 9 reconstructs the three-dimensional image data from the extracted tomographic image data associated with each oscillation angle. The reconstructed three-dimensional image data is outputted to the display device 5, so that the three-dimensional image of the tumor is displayed thereon.

As described above, according to the ultrasonic diagnostic apparatus 1, when the size (lateral width and longitudinal width) of the region of interest (ROI), the oscillation angle, the oscillation rate, and the size of the region of interest (ROI) associated with each oscillation angle are obtained from the size (lateral width, longitudinal width, and width in depth direction) of the tumor, it is possible to reconstruct the three-dimensional image data based on the shape of the tumor. Therefore, the ultrasonic diagnostic apparatus 1 can suitably extract and display the three-dimensional image of the tumor.

As in the example with respect to the mother and the unborn baby, the position of the region of interest (ROI) may be automatically determined by the ultrasonic diagnostic apparatus 1. For example, when the end points S10 and S20 shown in FIG. 10 are specified by the operator, the ROI position determining device 64 obtains the position (coordinates) of the center point of the lateral width D10 from the positions (coordinates) of the end points S10 and S20. Then, the ROI position determining device 64 determines the position (coordinates) of the center point of the region of interest (ROI) 26*a* based on the position (coordinates) of the center point of the lateral width D10 using the above-mentioned expression (3).

The example in which the mother and the unborn baby are subjected to image taking and the example in which the tumor is subjected to image taking are described in this embodiment. Even when another diagnostic region is subjected to image taking, the region of interest (ROI) and the oscillation angle which are suitable for the shape of the diagnostic region can be set by the ultrasonic diagnostic apparatus 1, so that a three-dimensional image of the diagnostic region can be preferably extracted and displayed. For example, even when an internal organ such as a heart or a liver is set as the diagnostic region, the region of interest (ROI) and the oscillation angle which are suitable for the shape of the heart or the like can be set by the ultrasonic diagnostic apparatus 1, so that a three-dimensional image of the heart or the like can be preferably extracted and displayed.

As described above, according to the ultrasonic diagnostic apparatus 1 in this embodiment, the size (lateral width and longitudinal width) of the diagnostic region are measured based on the tomographic image as the two-dimensional information. The size of the region of interest, the oscillation angle, and the oscillation rate (scanning line density) are determined based on the obtained values and the position of the interest. Therefore, it is possible to automatically determine the region of interest, the oscillation angle, and the oscillation rate (scanning line density), which are suitable to extract the image of the diagnostic region. Thus, the image necessary to observe the diagnostic region is efficiently obtained, with the result that the diagnostic efficiency using the ultrasonic diagnostic apparatus can be improved.

What is claimed is:

1. An ultrasonic diagnostic apparatus with a scanning device having a plurality of ultrasonic transducers arranged in a predetermined direction, for acquiring a three-dimensional ultrasonic image by scanning an ultrasonic wave in a three-dimensional imaging region of an object to be examined while the ultrasonic transducers are oscillated in a direction orthogonal to a scanning plane corresponding to the predetermined direction, comprising:
    a two-dimensional ultrasonic image acquiring device configured to acquire a two-dimensional ultrasonic image of a head of an unborn baby;
    an unborn baby development data obtaining device configured to obtain data relating to development information of an unborn baby based on a diameter of the acquired two-dimensional ultrasonic image of the head of the unborn baby having a longest lateral width;
    an ROI (region of interest) determination device configured to determine a size of a region of interest on the scanning plane, in proportion to a three dimensional size of the head of the unborn baby by determining the three dimensional size, including lateral width, longitudinal width, and width in a depth direction, of the head of the unborn baby based on the data relating to the development information of the unborn baby obtained by the unborn baby development data obtaining device;
    an oscillation device configured to oscillate the ultrasonic transducers through a variable angle range; and
    an angle range determination device configured to determine an angle range for oscillating the ultrasonic transducers in the direction orthogonal to the scanning plane, based on the determined size of the region of interest,
    wherein the scanning device is configured to acquire a three-dimensional ultrasonic image by scanning in an angle range determined according to the angle range determination device.

2. The ultrasonic diagnostic apparatus according to claim 1, further comprising:
    a displaying device configured to display the two-dimensional ultrasonic image generated according to the data acquired in advance by scanning the object to be examined,
    wherein the unborn baby development data obtaining device is configured to obtain the data relating to the development information of the unborn baby that has been specified by an operator via the ultrasonic image displayed by the displaying device.

3. The ultrasonic diagnostic apparatus according to claim 2, wherein the displaying device is configured to display the two-dimensional ultrasonic image of mother and the unborn baby acquired in advance by the scan to the body of the mother as the object to be examined.

4. The ultrasonic diagnostic apparatus according to claim 3, wherein,
    the unborn baby development data obtaining device is configured to obtain a shape of the head of the unborn baby, and
    the ROI determining device is configured to determine the size of the region of interest on the scanning plane based on the shape of the head of the unborn baby.

5. The ultrasonic diagnostic apparatus according to claim 4, wherein the angle range determination device is configured to determine an angle range for oscillating the ultrasonic transducers in the direction orthogonal to the scanning plane based on the determined size of the region of interest specified by an operator, the shape of the head of the unborn baby, and a position of the region of interest on the two-dimensional ultrasonic image.

6. The ultrasonic diagnostic apparatus according to claim 4, wherein the angle range determination device is configured to determine a width of the head of the unborn baby in a depth direction from the shape of the head of the unborn baby and to determine an angle range for oscillating the ultrasonic transducers in the direction orthogonal to the scanning plane based on the determined size of the region of interest specified by an operator, the shape of the head of the unborn baby, the width of the head of the unborn baby in the depth direction, and a position of the region of interest on the two-dimensional ultrasonic image.

7. The ultrasonic diagnostic apparatus according to claim 3, wherein,
the unborn baby development data obtaining device is configured to further obtain a longitudinal width of the head of the unborn baby from the two-dimensional ultrasonic image of the mother and the unborn baby, which is acquired in advance, and
the ROI determining device is configured to determine the size of the region of interest on the scanning plane based on the longitudinal width and the longest lateral width of the head of the unborn baby.

8. The ultrasonic diagnostic apparatus according to claim 1, further comprising:
a patient data processing device configured to obtain the number of weeks of pregnancy.

9. The ultrasonic diagnostic apparatus according to claim 1, wherein the angle range determination device is configured to determine the oscillating angle based on the region of interest determined by the ROI determination device.

10. The ultrasonic diagnostic apparatus according to claim 1, further comprising:
a memory device configured to store rates for oscillating the ultrasonic transducers in association with angle ranges for oscillating the ultrasonic transducers and information indicating image qualities,
wherein the angle range determination device is configured to determine an associated rate for oscillating the ultrasonic transducers, which is stored in the memory device, based on the determined angle range specified by an operator for oscillating the ultrasonic transducers and information indicating image quality.

11. An ultrasonic image acquiring method using a plurality of ultrasonic transducers arranged in a predetermined direction, for acquiring a three-dimensional ultrasonic image by scanning an ultrasonic wave in a three-dimensional imaging region of an object to be examined while the ultrasonic transducers are oscillated in a direction orthogonal to a scanning plane corresponding to the predetermined direction, comprising:
acquiring a two-dimensional ultrasonic image of a head of an unborn baby;
obtaining an unborn baby development data relating to the development information of the unborn baby based on a diameter of the acquired two-dimensional ultrasonic image of the head of the unborn baby having a longest lateral width;
determining in an ROI (region of interest) determination including, a size of a region of interest on the scanning plane, in proportion to a three dimensional size of the head of the unborn baby by determining the three dimensional size, including lateral width, longitudinal width, and width in a depth direction, of the head of the unborn baby based on the data relating to the development information of the unborn baby obtained by the unborn baby development data obtaining;
oscillating the ultrasonic transducers through a variable angle range; and
determining an angle range for oscillating the ultrasonic transducers in the direction orthogonal to the scanning plane, based on the determined size of the region of interest,
wherein a three-dimensional ultrasonic image is acquired by scanning in an angle range determined according to the angle range determining.

12. The ultrasonic image acquiring method according to claim 11, further comprising:
displaying the two-dimensional ultrasonic image generated according to the data acquired in advance by scanning the object to be examined,
wherein, in the unborn baby development data obtaining, the data relating to the development information of the unborn baby that has been specified by an operator is obtained via the ultrasonic image displayed during displaying.

13. The ultrasonic image acquiring method according to claim 12, wherein, during displaying, the two-dimensional ultrasonic image is displayed, the two-dimensional ultrasonic image being of mother and the unborn baby acquired in advance by the scan to the body of the mother as the object to be examined.

14. The ultrasonic image acquiring method according to claim 13, wherein,
in the unborn baby development data obtaining, a shape of the head of the unborn baby is obtained, and
in the ROI determining, the size of the region of interest on the scanning plane is determined based on the shape of the head of the unborn baby.

15. The ultrasonic image acquiring method according to claim 14, wherein, in the angle range determination, an angle range for oscillating the ultrasonic transducers in the direction orthogonal to the scanning plane is determined based on the determined size of the region of interest specified by an operator, the shape of the head of the unborn baby, and a position of the region of interest on the two-dimensional ultrasonic image.

16. The ultrasonic image acquiring method according to claim 14, wherein, in the angle range determining, a width of the head of the unborn baby in a depth direction is determined from the shape of the head of the unborn baby and an angle range for oscillating the ultrasonic transducers in the direction orthogonal to the scanning plane is determined based on the determined size of the region of interest specified by an operator, the shape of the head of the unborn baby, the width of the head of the unborn baby in the depth direction, and a position of the region of interest on the two-dimensional ultrasonic image.

17. The ultrasonic image acquiring method according to claim 11, wherein, in the unborn baby development data obtaining, the number of weeks of pregnancy is obtained as the data relating to the development information of the unborn baby.

18. The ultrasonic image acquiring method according to claim 11, wherein, in the angle range determination, the oscillating angle is determined based on the region of interest determined by the ROI determination.

19. The ultrasonic image acquiring method according to claim 11, wherein,
in the unborn baby development data obtaining, a longitudinal width of the head of the unborn baby is further obtained from the two-dimensional ultrasonic image of the mother and the unborn baby, which is acquired in advance, and in the ROI determination, the size of the region of interest on the scanning plane is determined based on the longitudinal width and the longest lateral width of the head of the unborn baby.

20. The ultrasonic image acquiring method according to claim 11, wherein, a memory device is used for storing rates for oscillating the ultrasonic transducers in association with angle ranges for oscillating the ultrasonic transducers and information indicating image qualities, and in the angle range determining, an associated rate for oscillating the ultrasonic transducers is determined based on the determined angle range specified by an operator for oscillating the ultrasonic transducers and information indicating image quality.

* * * * *